United States Patent [19]
Barron et al.

[11] Patent Number: 4,760,080
[45] Date of Patent: Jul. 26, 1988

[54] COMPOSITION FOR THE TEMPORARY STIMULATION OF URINE PRODUCTION

[76] Inventors: Larry Barron; Susan C. Barron, both of 7 Hamilton Ave., Winnipeg, MB, Canada, R2Y 2G4

[21] Appl. No.: 893,155

[22] Filed: Aug. 5, 1986

[30] Foreign Application Priority Data

Aug. 21, 1985 [CA] Canada ................... 489180

[51] Int. Cl.$^4$ ................... A61K 31/525; A61K 31/34
[52] U.S. Cl. ................... 514/251; 514/474; 514/904
[58] Field of Search ............ 514/904, 251, 474

[56] References Cited
U.S. PATENT DOCUMENTS

4,619,829  10/1986  Motschan ................... 514/904

Primary Examiner—Frederick E. Waddell
Attorney, Agent, or Firm—Gunars Gaikis

[57] ABSTRACT

The production of urine can be stimulated by a composition wherein a single dose comprises the following: 5 grams calcium ascorbate (ascorbic acid), 1,000 I.U. Vitamin E (d alpha tocopherol acetate), 1 gram pantothenic acid (calcium d-Pantothenate), 100 mg Vitamin $B_2$ (riboflavin), 100 mg Vitamin $B_6$ (pyridoxine hydrochloride), 25 mg Vitamin $B_1$ (thiamine), 2 grams potassium gluconate, a binder.

3 Claims, No Drawings

COMPOSITION FOR THE TEMPORARY STIMULATION OF URINE PRODUCTION

This invention is a non-toxic, non-allergenic formula that can be used by anyone, but it is specifically intended for hospital patients who are unable to urinate due to hospitalization, not due to a specific disease or to brain motor response damage.

A patient's system is below par after surgery. The patient has been subject to various medications, surgery, anesthetics, interims of inactivity, all of which tend to disrupt the normal routine of physical activity, sleep and intestinal mobility.

One common problem encountered during hospital recovery is poor urination or inability to urinate. Frequent urination is important after surgery and during hospital convalescence. The cells of the body rid themselves of accumulated wastes (i.e., by-products from the chemical reactions occuring in the cells). The destroyed tissue is broken down by enzyme activity and is excreted as waste product. A nitrogen-containing substance, urea, is the result of cell destruction. Urea can accumulate in the blood and become toxic if not eliminated. Excessive salt and water, if not urinated from the body, can increase the blood pressure. Removal of the wastes from the body by the kidneys (which filter the blood) eliminates the possibility of an accumulation of wastes in the cells. The hospital staff usually monitors the frequency of urination, as well as logging the amounts per day. Walking the patient as soon as possible after surgery and during the recovery period is a practice to try to re-establish the patient's normal bodily functions. Increasing the fluid intake substantially has also been tried to increase urine flow.

Patients with accumulated water and wastes are usually given diuretics which stimulate water excretion. A catheter is sometimes used on patients unable to pass urine. Catheters can be painful and discomforting; ensuing infections are not uncommon. Diuretics can cause various side effects, including kidney damage. Diuretics tend to increase the loss of all water soluble nutrients; in fact, the greater the liquid intake, the more water soluble nutrients are forced out of the body by diuretic action with the water-fluid loss. All the B vitamins as well as minerals such as potassium and magnesium are easily lost when diuretics are administered.

This new composition is not a diuretic; this composition stimulates urine production and enables urination to occur easily without adverse side effects. The invention overcomes past difficulties because the stimulation of urine is done without the loss of all water soluble nutrients. Kidney damage cannot occur from taking the formula. The formula will not interfere with medications.

The formula's components stimulate urine production in the following manner:

The formula has the ingredient Vitamin C (ascorbic acid) which is essential to prolong and enhance the effectiveness of adrenal cortisone production. If the adrenal hormones are produced adequately by the adrenal glands, urine production can be stimulated. The formula's ascorbic acid, although not essential to actual cortisone production, does prolong the cortisone hormone by delaying its breakdown. Pantothenic acid (calcium d pentothenate), Vitamin $B_6$ (pyridoxine hydrochloride), Vitamin $B_2$ (riboflavin), and Vitamin E (d alpha tocopherol acetate) have been included in the formula because they stimulate cortisone production. Also, the addition of Vitamin E and pantothenic acid decreases the need for ascorbic acid and increases its effectiveness. However, four to five grams of ascorbic acid are necessary for the formula to be effective, as explained in the following paragraphs.

It is common knowledge that ascorbic acid will combine with any foreign substances present in the blood. Foreign substances are matter such as drugs, wastes excreted from cells, chemical agents such as artificial sweeteners, lead, carbon tetrachloride, saccharine, and a multitude of others. The resultant combination of ascorbic acid with these foreign substances is referred to as ascorbigen. Many administered drugs cause the blood Vitamin C (ascorbic acid) levels to drop; some drugs destroy ascorbic acid present in the blood for weeks after the drugs are discontinued (e.g., some tranquilizers after prolonged use). Some doctors give ascorbic acid with medications to prevent liver damage. To compensate for that ascorbic acid which combines with the foreign substances to form ascorbigen, enough ascorbic acid must be provided in the formula to be used for cortisone production.

Accordingly, the present invention provides a composition for stimulating urine production in human beings comprising from 3 to 10 grams of calcium ascorbate, from 800 to 1,000 I.U. of Vitamin E, from 1 to 2 grams of pantothenic acid, from 75 to 100 mg of Vitamin $B_2$, from 75 to 100 mg of Vitamin $B_6$, from 25 to 50 mg of Vitamin $B_1$, and from 1 to 2 grams of potassium gluconate.

The present invention further provides for a method for stimulating urine production in human beings with diminished renal function comprising administering, all at one time, to such human being, the composition in the immediately aforesaid paragraph.

A preferred dose of the formula would be 5 grams of calcium ascorbate (ascorbic acid), 1,000 I.U. Vitamin E (d alpha tocopherol acetate), 1 gram pantothenic acid (calcium d-Pantothenate), 100 mg Vitamin $B_2$ (riboflavin), 100 mg Vitamin $B_6$ (pyridoxine hydrochloride), 25 mg Vitamin $B_1$ (thiamine), 2 grams potassium gluconate. To administer the formula, the $B_1$ (thiamine) $B_2$, $B_6$, pantothenic acid, and potassium gluconate may be in tablet form. The 5 grams of calcium ascorbate may be in tablet form or in powder form. The patient swallows the tablets with a glass of beverage of choice, preferably with a meal or snack, not on an empty stomach. To reduce the number of tablets that a patient has to swallow, the calcium ascorbate (ascorbic acid) in powder from to a 5 gram equivalent can be mixed into juice or water and drunk. It makes no difference as to the formula's effectiveness whether the patient takes a tablet form of calcium ascorbate or a powder form mixed in liquid.

It is best to take the formula twice a day—one dose in the morning and one dose later in the day. Usually, two doses are sufficient but a third dose could be taken if necessary.

A further to note to physicians administering this formula:

This formula contains ascorbic acid. If the patient is subject to a glucose tolerance or blood sugar test, the physician must be aware of the effect high blood levels of ascorbic acid can have on the readings of such tests. These tests can give false positives (indicative of diabetes) because high Vitamin C intake results in excretion of the sugar xylulose. To the most common glucose tolerance test, this sugar appears to be glucose in the urine, a symptom of diabetes. Vitamin C itself looks like sugar to the very commonly used orthotoluidine blood sugar test. Also, the glucose oxidase test gives the false abnormally low readings in the presence of high concentrations of antioxidants such as Vitamin C. Therefore, the physician may find it advisable to administer the hexokinase test for blood sugar or glucose tolerance measurements. The hexokinase test will give an accurate reading without the false positives caused by the high levels of Vitamin C. It should be noted that in most cases, the patients would not be on the formula long enough to cause the false readings on the usual blood sugar or glucose tolerance tests.

The embodiments of the invention in which an exclusive use or privilege is claimed are defined as follows:

1. A method for stimulating urine production in human beings with diminished renal function comprising administering, all at one time, to said human being, the composition comprising:
   from 3 to 10 grams of calcium ascorbate,
   from 800 I.U. to 1,000 I.U. of Vitamin E,
   from 1 to 2 grams of pantothenic acid,
   from 75 to 100 mg of Vitamin $B_2$,
   from 75 to 100 mg of Vitamin $B_6$,
   from 25 to 50 mg of Vitamin $B_1$ and
   from 1 to 2 grams potassium gluconate.

2. The method of claim 1 wherein the composition comprises:
   5 grams of calcium ascorbate,
   1,000 I.U. Vitamin E,
   1 gram of pantothenic acid,
   100 mg of Vitamin $B_2$,
   100 mg of Vitamin $B_6$,
   25 mg of Vitamin $B_1$, and
   2 grams potassium gluconate.

3. A method for stimulating urine production in a human being with diminished renal function comprising administering to said human being calcium ascorbate in an amount sufficient to inhibit the metabolism of cortisone hormone.

* * * * *